United States Patent
Talman et al.

(10) Patent No.: US 7,771,351 B1
(45) Date of Patent: Aug. 10, 2010

(54) METHOD AND APPARATUS FOR EDDY CURRENT COMPENSATION IN A RADIO FREQUENCY PROBE

(75) Inventors: James R. Talman, Crofton, MD (US); Aaron J. Fleischman, University Heights, OH (US); Brian L. Sauer, Parma, OH (US); Shuvo Roy, Shaker Heights, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 921 days.

(21) Appl. No.: 11/441,851

(22) Filed: May 26, 2006

Related U.S. Application Data

(60) Provisional application No. 60/685,720, filed on May 27, 2005.

(51) Int. Cl.
*A61B 5/07* (2006.01)
*A61B 5/00* (2006.01)
(52) U.S. Cl. .................. 600/302; 600/300; 600/301
(58) Field of Classification Search .................. None
See application file for complete search history.

(56) References Cited

U.S. PATENT DOCUMENTS

| | | | | |
|---|---|---|---|---|
| 3,651,398 A | * | 3/1972 | Urmenyi | 324/224 |
| 4,092,867 A | * | 6/1978 | Matzuk | 73/609 |
| 4,385,636 A | * | 5/1983 | Cosman | 600/561 |
| 4,453,162 A | * | 6/1984 | Money et al. | 340/870.39 |
| 4,593,703 A | * | 6/1986 | Cosman | 600/561 |
| 4,688,580 A | * | 8/1987 | Ko et al. | 600/547 |
| 5,412,182 A | * | 5/1995 | Chan | 219/635 |
| 5,626,630 A | * | 5/1997 | Markowitz et al. | 607/60 |
| 5,967,986 A | * | 10/1999 | Cimochowski et al. | 600/454 |
| 6,036,636 A | * | 3/2000 | Motoki et al. | 600/146 |
| 6,128,174 A | * | 10/2000 | Ritter et al. | 361/143 |

(Continued)

FOREIGN PATENT DOCUMENTS

EP 0 964 261 A2 12/1999

(Continued)

OTHER PUBLICATIONS

Baldi et al., "A Self-Resonant Frequency-Modulated Micromachined Passive Pressure Transensor", *IEEE Sensors Journal*, vol. 3, No. 6, Dec. 2003, pp. 728-733, XP-001047496 ISSN: 1530-437X.

(Continued)

*Primary Examiner*—Henry M Johnson, III
*Assistant Examiner*—Atia Syed
(74) *Attorney, Agent, or Firm*—Tarolli, Sundheim, Covell & Tummino LLP

(57) ABSTRACT

Systems and methods are provided for determining a characteristic of an associated in vivo sensor within a living body. A transmit coil produces an excitation signal, having a first orientation, to excite the in vivo sensor to produce a response signal. A receive coil produces a current in response to the response signal. The receive coil is oriented to interact with signals having a second orientation that is substantially orthogonal to first orientation. The probe further comprises at least one eddy current compensation coil that produces a compensation field. A component of the compensation field along the second orientation has a magnitude at the receive coil substantially equal and opposite to a magnitude of a similarly oriented component of a magnetic field associated with eddy currents induced within the body.

3 Claims, 3 Drawing Sheets

U.S. PATENT DOCUMENTS

| | | | |
|---|---|---|---|
| 6,164,284 A * | 12/2000 | Schulman et al. | 128/899 |
| 6,172,499 B1 * | 1/2001 | Ashe | 324/207.12 |
| 6,231,516 B1 * | 5/2001 | Keilman et al. | 600/485 |
| 6,351,048 B1 * | 2/2002 | Schob et al. | 310/90.5 |
| 6,363,276 B1 * | 3/2002 | Prem et al. | 607/6 |
| 6,473,652 B1 * | 10/2002 | Sarwal et al. | 607/62 |
| 6,579,235 B1 | 6/2003 | Abita et al. | |
| 6,682,480 B1 * | 1/2004 | Habib et al. | 600/300 |
| 6,766,200 B2 * | 7/2004 | Cox | 607/60 |
| 7,064,676 B2 * | 6/2006 | Hall et al. | 340/853.1 |
| 7,284,442 B2 * | 10/2007 | Fleischman et al. | 73/753 |
| 2002/0123777 A1 * | 9/2002 | Dolgin et al. | 607/60 |
| 2002/0147416 A1 | 10/2002 | Zogbi et al. | |
| 2003/0025503 A1 * | 2/2003 | Fanini et al. | 324/339 |
| 2004/0127895 A1 * | 7/2004 | Flock et al. | 606/41 |
| 2005/0010301 A1 * | 1/2005 | Disilvestro et al. | 623/18.12 |
| 2005/0107870 A1 * | 5/2005 | Wang et al. | 623/1.44 |
| 2005/0147512 A1 * | 7/2005 | Chen et al. | 417/423.12 |
| 2005/0165317 A1 * | 7/2005 | Turner et al. | 600/486 |
| 2005/0187488 A1 * | 8/2005 | Wolf | 600/561 |
| 2005/0283330 A1 * | 12/2005 | Laraia et al. | 702/104 |
| 2006/0074479 A1 * | 4/2006 | Bailey et al. | 623/1.13 |
| 2006/0211913 A1 * | 9/2006 | Dlugos et al. | 600/37 |
| 2006/0211914 A1 * | 9/2006 | Hassler et al. | 600/37 |
| 2008/0067874 A1 * | 3/2008 | Tseng | 307/104 |

OTHER PUBLICATIONS

Talman et al., "Orthogonal-Coil RF Probe for Implantable Passive Sensors", *IEEE Sensors Journal*, vol. 53, No. 3, Mar. 2006, pp. 538-546, XP-002407799, ISSN: 0018-9294.

* cited by examiner

METHOD AND APPARATUS FOR EDDY CURRENT COMPENSATION IN A RADIO FREQUENCY PROBE

RELATED APPLICATION

This application claims priority from U.S. provisional patent application Ser. No. 60/685,720, filed May 27, 2005, the subject matter of which is incorporated herein by reference.

FIELD OF THE INVENTION

The present invention relates to an apparatus and method for in vivo sensing and, in particular, is directed to a method and apparatus for determining a characteristic impedance of an in vivo sensor.

BACKGROUND OF THE INVENTION

Information regarding the conditions inside a body cavity in a patient, such as a human, can be very helpful to a physician treating the patient. For example, it is desirable to monitor intracranial pressure to look for problems such as hemorrhaging and tumors. As another example, it is also desirable to monitor the pressure inside various blood vessels in the human body to help determine if a problem, such as stenosis or an aneurysm, exists. Due to the difficulties of providing power to a device within the body, passive sensors are often used for in vivo sensing. Passive sensors can be fabricated to detect pressure, temperature, pH, etc, by causing one element of the resonant circuit to change in response to the quantity being detected. This changes the resonant frequency of the device, and this change in resonant frequency can be detected externally using a radiofrequency (RF) probe.

Microelectromechanical systems, or MEMS, are a class of miniature electromechanical components and systems that are fabricated using techniques originally developed for fabricating microelectronics. MEMS devices, such as pressure sensors and strain gauges, manufactured using microfabrication and micromachining techniques can exhibit superior performance compared to their conventionally built counterparts, and are resistant to failure due to fatigue, corrosion, etc. Further, due to their extremely small size, MEMS devices can be utilized to perform functions in unique applications, such as sensing conditions within the human body, that were not previously feasible using conventional devices Recently there has been considerable interest in exploiting microelectromechanical system (MEMS) technology to simplify the fabrication and reduce the cost of in vivo sensors. In many implementations, the RF probe used to detect the resonant frequency of a passive sensor uses a "grid-dip oscillator" approach. An oscillating RF current flows through an RF coil, inducing currents in the inductance coil of a nearby sensor. The loading effect of the sensor on the RF transmit coil results in a decrease or "dip" in the phase response of the transmitter current and the frequency at which this occurs is used to deduce the value of the quantity being measured. This method benefits from the simplicity of a single RF coil, but frequency measurements are complicated by difficulties associated with separating the small receive signal from the large oscillation signal.

SUMMARY OF THE INVENTION

In accordance with one aspect of the present invention, a radio frequency (RF) probe assembly is provided for determining a characteristic of an associated in vivo sensor within a living body. A transmit coil produces an excitation signal, having a first orientation, to excite the in vivo sensor to produce a response signal. A receive coil produces a current in response to the response signal. The receive coil is oriented to interact with signals having a second orientation that is substantially orthogonal to first orientation. The assembly further comprises at least one eddy current compensation coil that produces a compensation field. A component of the compensation field along the second orientation has a magnitude at the receive coil substantially equal and opposite to a magnitude of a similarly oriented component of a magnetic field associated with eddy currents induced within the body.

In accordance with another aspect of the invention, a radio frequency (RF) probe assembly is provided for determining a characteristic of an associated in vivo sensor within a living body. A transmit element produces an excitation signal, having a first orientation, to excite the in vivo sensor to produce a response signal. A receive element produces a current in response to the response signal. The receive coil is oriented to interact with signals having a second orientation that is substantially orthogonal to first orientation. The assembly further includes at least one eddy compensation element that produces a compensation field to counter the effects of magnetic eddy currents within the body. The compensation field is produced passively via a current inducted in the eddy current compensation element by at least one of the excitation signal, the eddy currents, or the response signal.

In accordance with yet another aspect of the present invention, a method is provided for operating an RF probe to determine a characteristic of an associated in vivo sensor in a living body. A transmit field is generated. The transmit field is operative to induce a response signal in an associated in vivo sensor. The response signal is received at a receiving element, having an associated orientation. A compensation field is produced to counter the effects of magnetic eddy currents within the body at an eddy current compensation element. The position of the eddy current compensation element is adjusted to maintain a component of the compensation field associated with the orientation of the receiving element at a magnitude substantially equal and opposite to a magnitude of a magnetic field component associated with eddy currents induced within the body. Accordingly, the compensation field component and the magnetic field component associated with the eddy currents cancel at the receiving element.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF EMBODIMENTS

The present invention relates to an apparatus and method for in vivo measurement of one or more characteristics of interest and, in particular, is directed to a method and apparatus for interrogating an in vivo sensor to determine a desired characteristic. Potential biomedical applications for the present invention include blood flow and pressure sensors in the vicinity of stents, intraocular pressure sensing for detection of glaucoma, pressure, or strain sensors for assessing the progress of spinal fusion procedures, and pressure sensors for monitoring a patient during treatment of hydrocephalus and abdominal aortic aneurysms.

Figure 1:
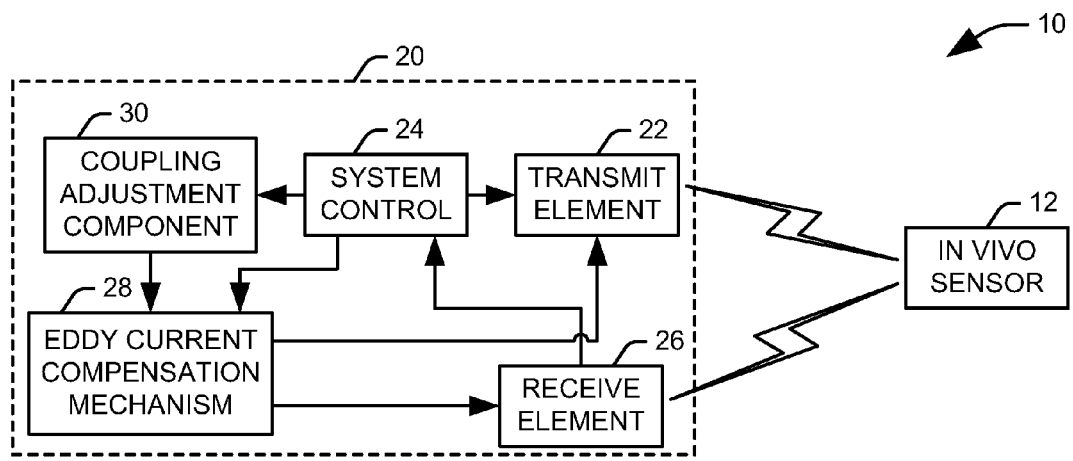
FIG. 1 illustrates a system for determining a characteristic of an in vivo sensor in accordance with an aspect of the present invention.

As representative of the present invention, FIG. 1 illustrates a system 10 for determining a characteristic of an in vivo sensor 12 implanted in a living body. For example, the in vivo sensor 12 can comprise a tank circuit sensor having an impedance, capacitance, inductance, or associated quality factor dependent on an internal characteristic of the body in which it is implanted, such as pressure. The quality factor may be that of an inductor, capacitor or a resonant circuit. The system includes an RF probe assembly 20 that excites the in vivo sensor 12 and detects a response signal from the sensor. This response signal is analyzed at the probe to determine a desired characteristic of the sensor 12.

The RF probe 20 includes a transmit element 22 that provides an excitation signal to the sensor 12 at a frequency determined by a system control 24. For example, the excitation signal can comprise a magnetic field or electromagnetic radiation having a first associated orientation. The excitation signal is received at the in vivo sensor 12, which produces a response signal. For example, the excitation signal can induce the response signal in the in vivo sensor. The power of the response signal will reach a maximum when the frequency of the excitation signal equals the resonant frequency of the sensor 12. The resonant frequency of the sensor 12 can, in turn, be function of the characteristic impedance and/or capacitance of the sensor 12. The response signal is then received at a receive element 26, oriented to receive fields or signals having a second orientation, and provided to the system control 24 for analysis. The second orientation is roughly orthogonal to the first orientation associated with the transmit element.

Accordingly, the system control 24 can sweep the frequency of the excitation signal through a frequency range of interest. As discussed above, the power of the response signal will increase as the frequency of the excitation signal approaches the resonant frequency of the sensor 12. The system control 24 can record the power of the response signal at each excitation frequency across the frequency range of interest. The resulting frequency response will have a peak near the resonant frequency of the sensor 12 and a reasonably flat response elsewhere, forming a reasonably level noise floor at the remaining frequencies. The width of the peak within the frequency response is a function of a quality factor associated with the in vivo sensor 12. Accordingly, the quality factor can be determined according to an appropriate measure of the peak width (e.g., peak width at half maximum). Among other factors, the noise floor represents coupling between the receive element 26 and the transmit element 22. When the RF probe 20 is placed in close proximity to conductive media, as are present in a human body, there is additional coupling between transmit and receive elements 22 and 26 due to magnetic eddy currents induced in any conductive media in the body. The eddy currents can severely degrade the isolation between the two elements. When the response signal is has a small peak magnitude, as might be provided by a small sensor, the increase in the noise floor caused by the eddy currents can obscure the frequency response peak, making a determination of the sensor impedance impossible.

In accordance with an aspect of the present invention, an eddy current compensation mechanism 28 is provided to mitigate the effects of the eddy currents on the isolation of the transmit and receive elements 22 and 26. For example, the eddy current compensation mechanism 28 can comprise one or more conductive coils placed on the RF probe 20 that produce an induced current in response to at least one of the excitation signal, the eddy currents, and the response signal. The induced current within the compensation coils produces a magnetic field having a first component oriented along the second orientation, associated with the receive element 26. The respective positions of the one or more compensation elements 28 can be selected via a coupling adjustment component 30 such that at the receive element 26, the magnitude of the first magnetic field component is equal to a similarly oriented magnetic field produced by the eddy currents. Accordingly, the effect of the eddy currents on the response signal received at the receive element 26 can be mitigated.

Alternatively, the compensation mechanism 28 can comprise compensation circuitry that provides a compensation signal to the response element 26. The compensation signal can be determined, for example, as a function of the excitation signal. In one implementation, the compensation circuitry includes a plurality of buffers that scale and delay the excitation signal to produce the compensation signal. It will be appreciated, however, that other implementations are feasible. It will further be appreciated that the compensation circuitry can be utilized in combination with one or more eddy compensation coils to mitigate the effects of the eddy currents.

Figure 2:
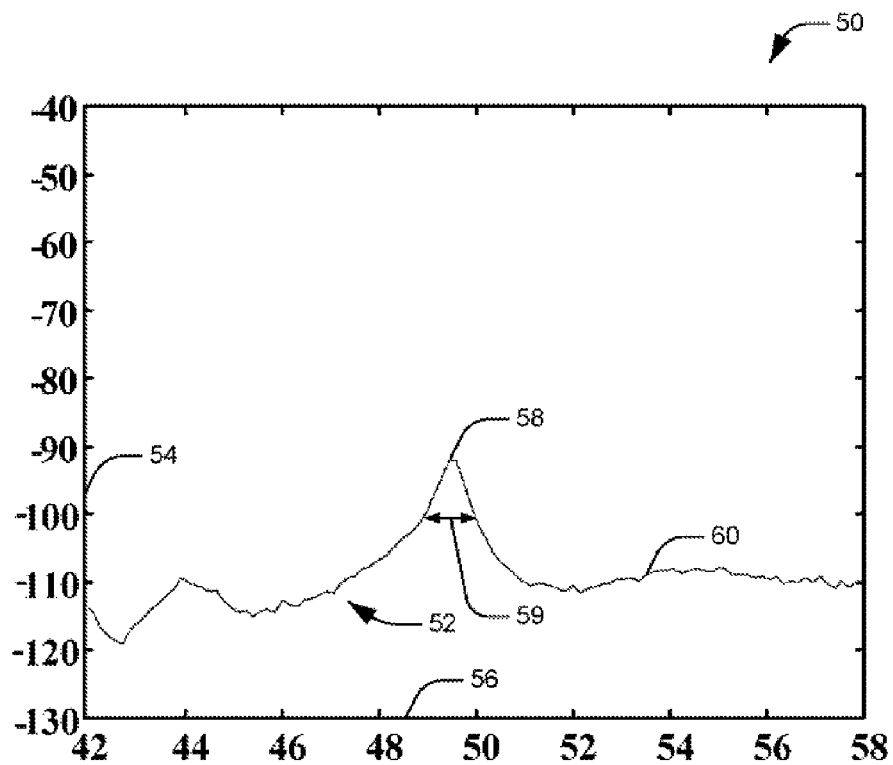
FIG. 2 illustrates a chart of an exemplary frequency response of an in vivo sensor to an excitation signal from an associated probe in accordance with an aspect of the present invention.

FIG. 2 illustrates a chart 50 of an exemplary frequency response 52 of an in vivo sensor to an excitation signal from an associated probe in accordance with an aspect of the present invention. The frequency response 52 is plotted on a vertical axis 54, representing the magnitude, $V_{out}$, of the response in decibels (dB) relative to a reference magnitude, $V_{ref}$, and a horizontal axis 56, representing the frequency of the excitation signal in MHz. The frequency response 52 rises to a peak power 58 at a resonant frequency, $f_r$. The peak associated with the resonant frequency has an associated peak width 59 that is a function of a quality factor associated with the in vivo sensor. At all other points, the frequency response remains at or around a noise floor 60 associated with the probe. Accordingly, an analysis of the frequency response 52 for the probe can provide an indication of a level of noise associated with the probe, the resonant frequency of the sensor, and the quality factor associated with the sensor. One or more characteristics of the environment in which the in vivo sensor is implanted can be determined from these qualities according to the design of the in vivo sensor.

Figure 3:
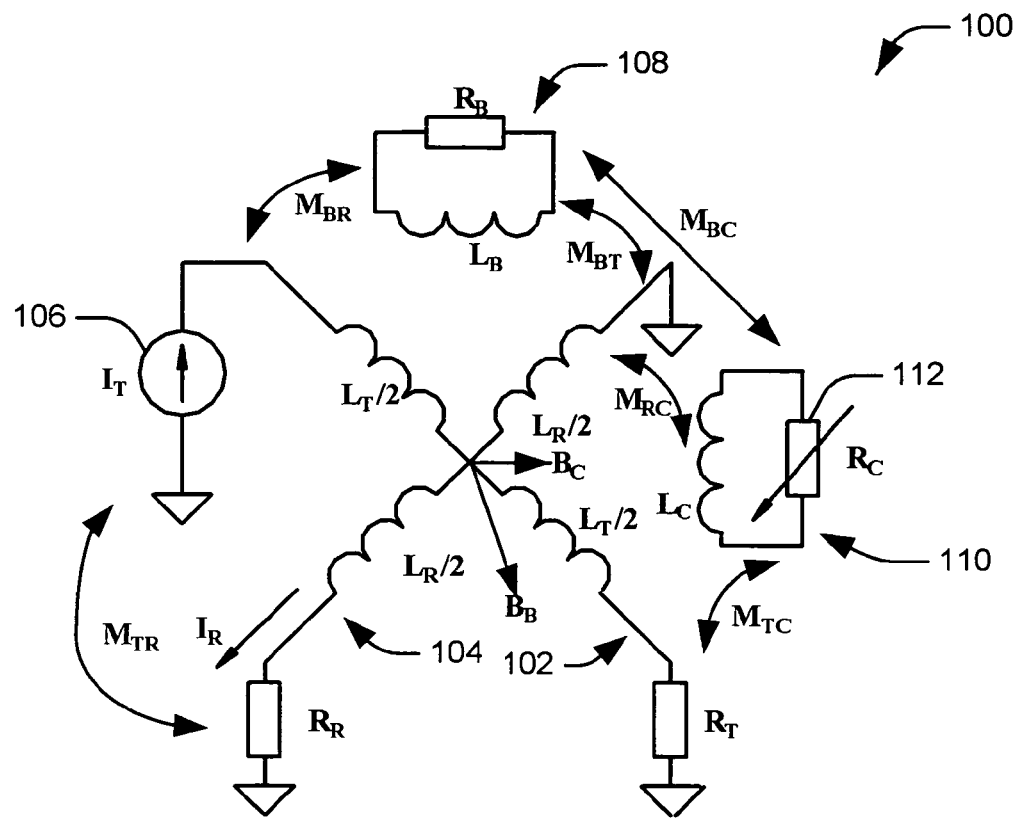
FIG. 3 illustrates an exemplary embodiment of an RF probe in accordance with an aspect of the present invention.

FIG. 3 illustrates an exemplary embodiment of an RF probe 100 in accordance with an aspect of the present invention. The probe 100 consists of two orthogonal coils, a transmit coil 102 and a receive coil 104. A swept-frequency transmit signal from a system control is applied as to the transmit coil 102, and a response signal received at the receive coil 104 is displayed. In the absence of a nearby resonator, the response signal is a greatly reduced version of the transmit signal due to the inherent spatial isolation between the orthogonal transmit and receive coils 102 and 104. Since it is preferable to minimize the size of sensors used inside of the human body, it is important to mitigate coupling between the loops so that the probe 100 can measure the relatively weak response signal that can be expected from smaller sensors.

The coils 102 and 104 may be modeled, as a practical matter, as inductor-resistor pairs having inductances of $L_T$ and $L_R$ and resistances of $R_T$ and $R_R$, respectively. The transmit coil 102 is provided with a current from a current source 106 such that current flows along a desired current polarity for the coil. Similarly, the response signal induces a current, and a corresponding current polarity, in the receive coil 104. The body 108 in which the in vivo sensor is implanted can also be modeled as a resistor-inductor pair with resistance $R_B$ and inductance $L_B$. It will be appreciated that each coil (e.g., 102) has a mutual inductance to the other coil (e.g., 104) and to the eddy current circuits produced in the body 108. For example, a first mutual inductance, $M_{TR}$, can be present between the transmit coil 102 and the receive coil 104, a second mutual inductance, $M_{BT}$, can be present between the transmit coil 102 and the body 108, and a third mutual inductance, $M_{BR}$, can be present between the receive coil 104 and the body 108. The eddy currents produce a magnetic field, $B_B$, at the center of the receive coil 104. This magnetic field can cause additional coupling between the coils 102 and 104, disrupting reception of the response signal at the coil 104.

In accordance with an aspect of the present invention, the probe 100 can include an eddy current compensation coil 110 that mitigates the effects of the eddy currents at the receive coil 104. Like the other coils 102 and 104, the eddy current compensation coil 110 can be modeled as a resistor-inductor pair with resistance $R_C$ and inductance $L_C$. The magnetic fields produced by the transmit coil 102, receive coil 104, and the body 106 each induce currents in the compensation coil 110 as a result of respective mutual inductances, M producing a magnetic field denoted by $B_C$. Accordingly, the compensation coil 110 can operate passively, via inducted current, to compensate for the eddy currents produced by the conductive body 108. Ideally, the component of $B_C$ normal to the receive coil 104 cancels the component of $B_B$ normal to the receive coil 104, resulting in zero received signal.

To achieve cancellation of the eddy current field, the normal component of $B_C$ must have the same magnitude and phase as the normal component of $B_B$. The temporal response of the body eddy currents can be modeled as an infinite sum of simple exponential responses, having appropriate magnitudes and time constants. At sufficiently low frequencies, the response is typically dominated by a single exponential characteristic. Neglecting $M_{TR}$ and $M_{BC}$, the two conditions for the compensation coil 100 to negate the effect of the eddy currents at the receive coil 104 are given by $$M_C^2 L_B = |M_{BR} M_{BT}| L_C$$
$$\frac{L_B}{R_B} = \frac{L_C}{R_C}.$$

The first condition can be satisfied by moving the compensation coil 110 to adjust the value of $M_C$. For example, the probe 100 can include a coupling adjustment component (not shown) that moves the compensation coil relative to the receive coil 104. Alternatively, the position of the compensation coil can remain fixed while the position of the probe is moved relative to the body to adjust the values of $M_{BR}$ and $M_{BT}$. The second condition is satisfied by including a potentiometer 112 or other variable resistor in the compensation loop to vary the value of $R_C$.

In an exemplary implementation, the RF probe 100 can be implemented in a polycarbonate or Teflon form. Orthogonal grooves can be provided on a surface of the form. A conducting material, such as a coaxial cable or copper wire, can be placed within the grooves to form conducting loops. For example, conductive material can be placed into a pair of orthogonal grooves to form the transmit and the receive coils 102 and 104. Similarly, one or more eddy current compensation coils (e.g., 110) can be implemented in the same manner.

Figure 4:
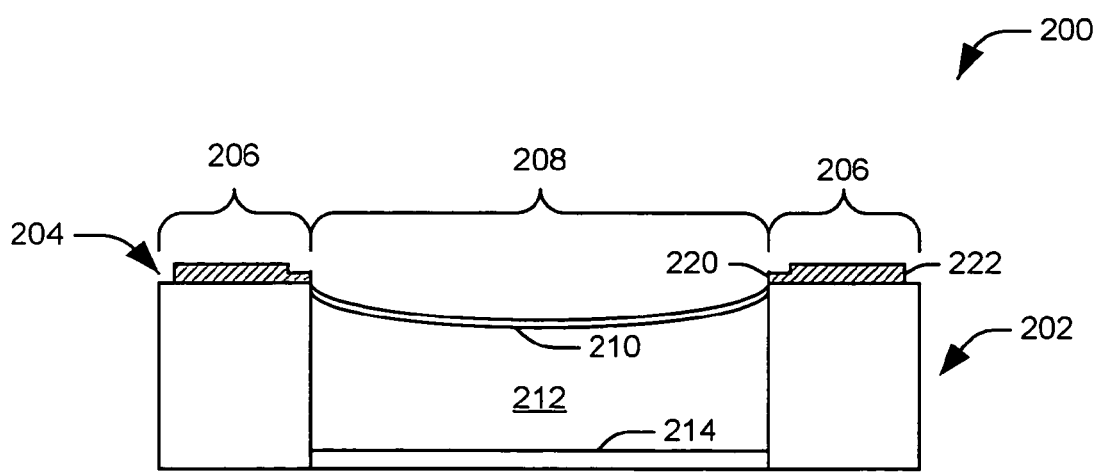
FIG. 4 illustrates an exemplary in vivo sensor in accordance with an aspect of the present invention.

FIG. 4 illustrates an exemplary in vivo sensor 200 in accordance with an aspect of the present invention. The illustrated sensor 200 is a pressure sensor, but the specific application and purpose of the sensor can vary in accordance with the present invention. The sensor includes a substrate 202 that can be comprised of a silicon material, but it will be appreciated that other materials may be used. The substrate 202 includes a contact surface 204 for making contact with a medium to be measured. For example, the contact surface 204 can be exposed to blood within an aneurysm sac or to aqueous humor within an eye. The surface 204 includes an outer non-compliant region 206 and an inner compliant region 208 that can be fabricated, for example, using MEMS techniques, as an impedance element, the impedance of which varies as the inner compliant region 208 changes shape. The compliant region 208 comprises a diaphragm 210 as one plate of a capacitive element that is separated by a dielectric 212 from another plate 214 of the capacitive element. As the pressure of the medium increases, the diaphragm plate 210 flexes closer to the other non-compliant plate 214 to change the capacitance of the capacitive element in proportion to the pressure exerted on the diaphragm plate 210. In the illustrated embodiment, the dielectric comprises air, but other suitably compliant dielectrics for example, hydrogel, silicone, and various high dielectric oils, may also be used, without deviating from the principles of the present invention.

A region of conductive material 220 can be included as part of the substrate 202. The conductive material 220 is electrically coupled to the impedance element of the compliant region 208 (e.g., at the diaphragm 210) which is a capacitive element. The conductive material 220 is responsive to an external signal for energizing the impedance element so that the pressure may be determined. For example, the region of conductive material 220 can comprise an inductor coil 222 fabricated in the non-compliant region 206 of the contact surface 204 such that it is electrically coupled to the capacitive element to form a resonance or tank circuit In the present embodiment, the inductor coil 222 is formed by disposing conductive material in a predetermined pattern, like a concentric spiraled pattern, for example, in the non-compliant region 206. It should be understood that the inductor region need not be embodied solely at the non-compliant region 206 and may be embodied as part of the compliant region 208 as well without deviating from the principles of the present invention. In accordance with an aspect of the present invention, the resonant circuit comprising the inductor coil 222 and the capacitive element formed by the plates 210 and 214 may be excited into resonance by an external electromagnetic signal in the radio frequency (RF) range. Tank circuits of this type have a natural resonant frequency $f_o$ that, to the first order, depends of the values of the inductor and the capacitor as follows:

$$f_o = 1/2\pi (LC)^{1/2}$$

where L is the inductance and C is the capacitance.

Accordingly, as the capacitance of the sensor 200 changes, the resonant frequency $f_o$ of the tank circuit will change in proportion thereto.

Figure 5:
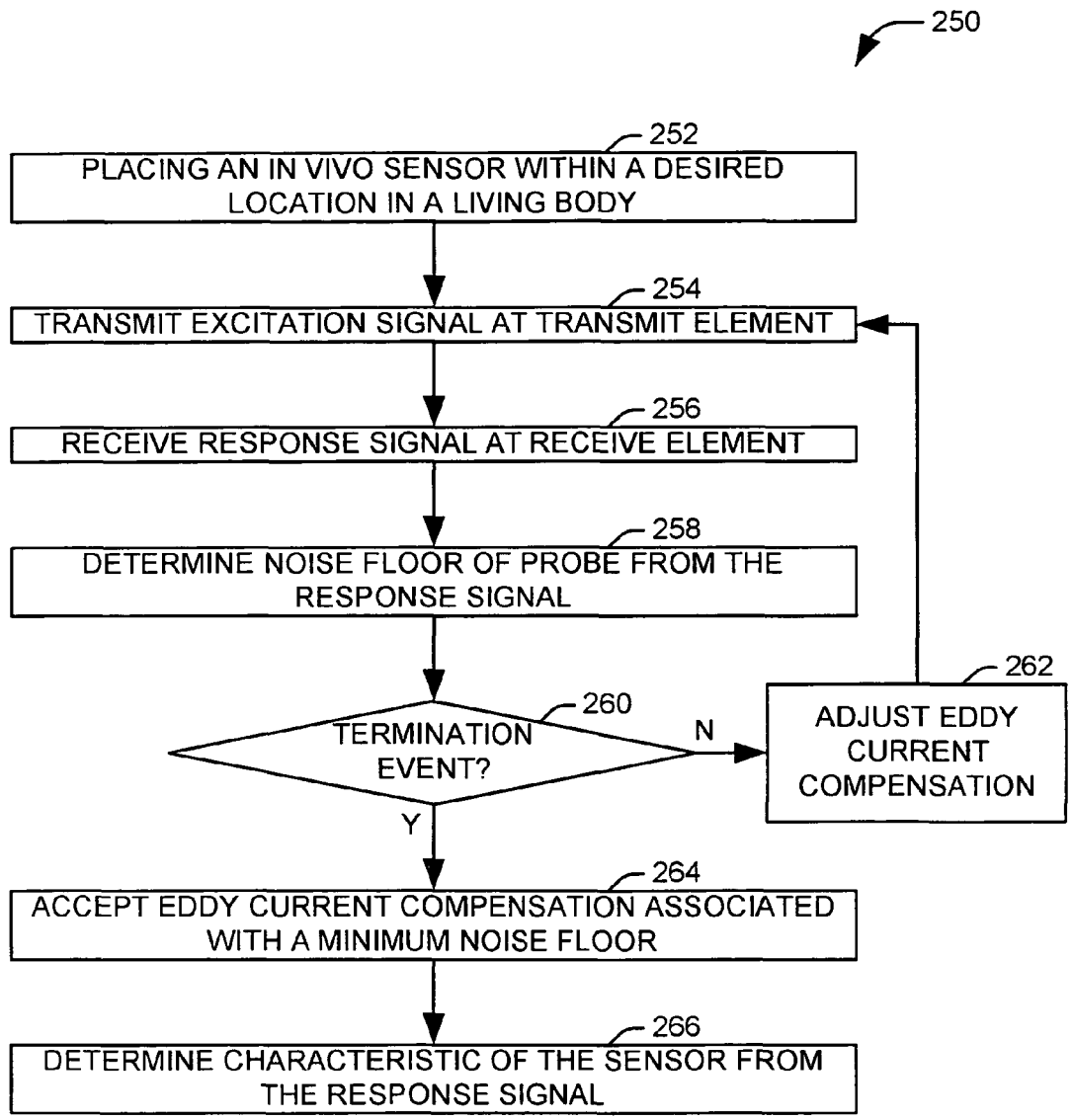
FIG. 5 illustrates an exemplary methodology for determining a characteristic of an in vivo sensor in accordance with an aspect of the present invention.

FIG. 5 illustrates an exemplary methodology 250 for determining a characteristic of an in vivo sensor in accordance with an aspect of the present invention. At step 252, the in vivo sensor is implanted at a desired location within a living body. For example, the sensor can be implanted within an aneurysm sac, in the aqueous humor of a human eye, inside of a hydrocephalic shunt, within an artificial joint, or along the surface of an orthopedic implant.

At step 254, a transmit signal, having a first orientation, is produced at a transmit element on a radio frequency (RF) probe. For example, the transmit element can provide an excitation signal that sweeps across a plurality of frequencies within a frequency range of interest. The excitation signal induces a response signal at the in vivo sensor. It will be appreciated that the magnitude of the response signal will approach a maximum value when the frequency of the excitation signal approaches a resonant frequency of the sensor. At other excitation frequencies, the response signal will remain at an associated noise floor. This noise floor is indicative of the degree of coupling between the transmit element and a receive element associated with the RF probe.

The response signal is received at the receive element at step 256. It will be appreciated that the receive element can have an associated second orientation that is substantially orthogonal to the first orientation, such that it is operative to receive signals having an orientation that is orthogonal or nearly orthogonal to the orientation of the excitation signal. The response signal can be analyzed at step 258 to determine a noise floor for the signal. At 260, it is determined if a termination event has occurred. For example, the termination event can comprise the achievement of a noise floor that falls below a predetermined threshold or a predetermined number of measurements of the noise floor.

If the termination event has not occurred (N), an eddy compensation associated with the RF probe is adjusted at step 262. For example, one or more eddy current compensation coils can be moved relative to the receive coil to adjust the magnitude of a magnetic field associated with the eddy current compensation coils at the receive coil. Similarly, the entire probe can be moved relative to the body to adjust the magnitude of a magnetic field component associated with the induced eddy currents at the receive coil. Alternatively, an eddy current compensation signal associated with the RF probe can be adjusted by changing one or more scaling or delay parameters associated with the signal. Accordingly, it will be appreciated that the effective position of the coil can be adjusted mechanically, electronically, or manually. Once the eddy current compensation has been adjusted, the methodology returns to step 254 to measure the noise floor of the probe. If the termination event has occurred (Y), the methodology advances to step 264, where an optimal eddy current compensation associated with a minimum noise floor is accepted. Once an optimal compensation has been selected, a desired characteristic of the sensor, such as an associated impedance, capacitance, or quality factor, can be determined from the response signal at step 266.

From the above description of the invention, those skilled in the art will perceive improvements, changes, and modifications. For example, it is contemplated that the present invention could be adapted to diagnose a number of degenerative eye disorders by measuring other characteristics of various structures of the eye, both within and external to the retina. Such improvements, changes, and modifications within the skill of the art are intended to be covered by the appended claims.

Having described the invention, we claim:

1. A radio frequency (RF) probe assembly for determining a characteristic of an associated in vivo sensor within a living body, comprising:
   a transmit coil that produces an excitation signal, having a first orientation, to excite the in vivo sensor to produce a response signal;
   a receive coil that produces a current in response to the response signal, the receive coil being oriented to interact with signals having a second orientation that is substantially orthogonal to first orientation;
   at least one eddy current compensation coil that produces a compensation field, a component of the compensation field along the second orientation having a magnitude at the receive coil substantially equal and opposite to a magnitude of a similarly oriented component of a magnetic field associated with eddy currents induced within the body; and
   a coupling adjustment component that adjusts the position of a given eddy current compensation coil of the at least one eddy compensation coil.

2. The assembly of claim 1, wherein the coupling adjustment component adjusts the position of the given eddy current compensation coil relative to the receive coil as to adjust the magnitude of the compensation field at the receive coil.

3. The assembly of claim 1, wherein the coupling adjustment component adjusts the position of the RF probe relative to the body as to adjust the magnitude of the magnetic field component associated with the induced eddy currents at the receive coil.

\* \* \* \* \*